US008538777B1

(12) United States Patent
Kaye et al.

(10) Patent No.: US 8,538,777 B1
(45) Date of Patent: Sep. 17, 2013

(54) SYSTEMS AND METHODS FOR PROVIDING PATIENT MEDICATION HISTORY

(75) Inventors: Elizabeth S. Kaye, Suwanee, GA (US); Reed Liggin, Canton, GA (US); John Taylor Dennis, Marietta, GA (US); Sean Daniel Reisz, Winston, GA (US); Jeffrey Scott Sauers, Suwanee, GA (US); Jessica Landisman Williams, Decatur, GA (US); Charles David Smith, Scottdale, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 977 days.

(21) Appl. No.: 12/165,031

(22) Filed: Jun. 30, 2008

(51) Int. Cl.
G06Q 50/00 (2012.01)
(52) U.S. Cl.
USPC ........................................ 705/3; 705/2; 705/4
(58) Field of Classification Search
USPC .................................................... 705/2/3, 2–4
See application file for complete search history.

(56) References Cited

U.S. PATENT DOCUMENTS

| | | | |
|---|---|---|---|
| 4,674,041 A | 6/1987 | Lemon et al. |
| 4,723,212 A | 2/1988 | Mindrum et al. |
| 4,910,672 A | 3/1990 | Off et al. |
| 5,007,641 A | 4/1991 | Seidman |
| 5,080,364 A | 1/1992 | Seidman |
| 5,173,851 A | 12/1992 | Off et al. |
| 5,201,010 A | 4/1993 | Deaton et al. |
| 5,235,702 A | 8/1993 | Miller |
| 5,237,620 A | 8/1993 | Deaton et al. |
| 5,301,105 A | 4/1994 | Cummings, Jr. |
| 5,305,196 A | 4/1994 | Deaton et al. |
| 5,327,508 A | 7/1994 | Deaton et al. |
| 5,359,509 A | 10/1994 | Little et al. |
| 5,388,165 A | 2/1995 | Deaton et al. |
| 5,430,644 A | 7/1995 | Deaton et al. |
| 5,448,471 A | 9/1995 | Deaton et al. |
| 5,465,286 A | 11/1995 | Clare et al. |
| 5,544,044 A | 8/1996 | Leatherman |

(Continued)

FOREIGN PATENT DOCUMENTS

| CA | 2482370 A1 | 3/2006 |
|---|---|---|
| EP | 1310895 A2 | 11/2002 |

(Continued)

OTHER PUBLICATIONS

Hutty, S. (2002). Third party issues: Understanding drug benefits for better patient care. Pharmacy Practice, 18(6), CE1-CE16. Retrieved from http://search.proquest.com/docview/232078749?accountid=14753.*

(Continued)

*Primary Examiner* — Mark Holcomb
(74) *Attorney, Agent, or Firm* — Sutherland Asbill & Brennan LLP

(57) ABSTRACT

Systems and methods may be provided for obtaining and providing patient medication history. The systems and methods may include receiving a request for medication history information of a patient, the request including identification information for the patient. At least one memory may be accessed utilizing at least a portion of the identification information, the at least one memory including information associated with pharmacy claims transactions stored in the at least one memory in near real time as the pharmacy claims transactions are processed. Information associated with the medication history of the patient is obtained from the at least one memory and communicated in response to the received request.

17 Claims, 14 Drawing Sheets

(56) References Cited

U.S. PATENT DOCUMENTS

| | | |
|---|---|---|
| 5,550,734 A | 8/1996 | Tarter et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,644,778 A | 7/1997 | Burks et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A * | 12/1998 | Mayaud ........................... 705/3 |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,427,020 B1 | 7/2002 | Rhoads |
| 6,484,146 B2 | 11/2002 | Day et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,046,789 B1 | 5/2006 | Anderson et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 2001/0001014 A1 | 5/2001 | Akins, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0035484 A1* | 3/2002 | McCormick ........................ 705/2 |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0175929 A1 | 11/2002 | Hunt et al. |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0074218 A1 | 4/2003 | Liff et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0158755 A1* | 8/2003 | Neuman ........................... 705/3 |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0054657 A1 | 3/2004 | Takeyama |
| 2004/0073457 A1 | 4/2004 | Kalies |
| 2004/0078234 A1 | 4/2004 | Tallal, Jr. et al. |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0172281 A1 | 9/2004 | Stanners |
| 2004/0188998 A1 | 9/2004 | Henthorn |
| 2004/0249745 A1 | 12/2004 | Baaren |
| 2005/0015280 A1 | 1/2005 | Gabel et al. |
| 2005/0033604 A1 | 2/2005 | Hogan |
| 2005/0033610 A1 | 2/2005 | Cunningham |
| 2005/0060201 A1 | 3/2005 | Connely, III et al. |
| 2005/0065821 A1 | 3/2005 | Kalies |
| 2005/0086081 A1 | 4/2005 | Brock-Fisher |

| | | |
|---|---|---|
| 2005/0090425 A1 | 4/2005 | Reardan et al. |
| 2005/0102169 A1 | 5/2005 | Wilson |
| 2005/0125292 A1 | 6/2005 | Kassab et al. |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0240473 A1 | 10/2005 | Ayers et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0085230 A1 | 4/2006 | Brill et al. |
| 2006/0149587 A1 | 7/2006 | Hill, Sr. et al. |
| 2006/0149784 A1 | 7/2006 | Tholl et al. |
| 2006/0178915 A1* | 8/2006 | Chao ................................ 705/4 |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0247948 A1 | 11/2006 | Ellis et al. |
| 2006/0259363 A1 | 11/2006 | Jhetam |
| 2006/0271398 A1 | 11/2006 | Belcastro |
| 2006/0271405 A1 | 11/2006 | Cipolle et al. |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0067186 A1* | 3/2007 | Brenner et al. .................. 705/2 |
| 2007/0088576 A1 | 4/2007 | de Beus et al. |
| 2007/0124177 A1 | 5/2007 | Engleson et al. |
| 2007/0136100 A1 | 6/2007 | Daugherty et al. |
| 2007/0179957 A1 | 8/2007 | Gibson et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2010/0122202 A1 | 5/2010 | Omiya |

FOREIGN PATENT DOCUMENTS

| | | |
|---|---|---|
| WO | 9106917 A1 | 5/1991 |
| WO | 95/03569 A3 | 2/1995 |
| WO | 9725682 A1 | 7/1997 |
| WO | 9850871 A1 | 11/1998 |
| WO | 0039737 A1 | 7/2000 |
| WO | 2007025295 A2 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 13/181,082 mailed Feb. 20, 2013.

Final Office Action for U.S. Appl. No. 13/181,082 mailed Jul. 24, 2013.

* cited by examiner

RelayHealth

| REQUEST HISTORY | RESPONSE SEARCH | REPORTS | ADMINISTRATION | HELP | LOGOUT |

Medication History

HOME | REQUEST HISTORY

YOU ARE LOGGED IN AS salesdemosales.demo

Prescription Detail

Format: [PDF Format ▼] Export | Print ← 1105

Return to Request Result

Sort by: [Drug by Date ▼] ← 1115

↗ 1120
Patient Name: jane doe  Date Submitted: 04/15/2008
Date of Birth: 01/16/1972  Zip: 3034033838
Gender: Female  Cardholder Id:

Prescription
Label | Quantity | Fill Date | Days Supply | Refill #
SKELAXIN Tablet 800 mg | 30 | | | 2

Associated Physician
Physician ID | Name | Address | City | State | Zip code | Pharmacy
6641528925001 | Majella, Robert | Allscripts Lane | Libertyville | IL | 60048 | Druglix
 | | | | | | 333 SR 566
 | | | | | | Providence, RI
 | | | | | | 02903
 | | | | | | 4015633390
 | | | | | | Phone
 | | | | | | 8478889999 ← 1110

SYSTEMS AND METHODS FOR PROVIDING PATIENT MEDICATION HISTORY

FIELD OF THE INVENTION

Aspects of the invention relate generally to medication history, and more particularly, to systems and methods for providing patient medication history to healthcare service providers.

BACKGROUND OF THE INVENTION

Healthcare service providers, such as, hospitals, doctor offices, etc., often collect information associated with the medication history of their patients. Such information is utilized in the diagnosis of a patient's medical condition and in determining the most appropriate courses of actions for treatment of the patient. Additionally, in the case of hospitals, the collection of medication history for a patient is often required in order to satisfy standards established by the Joint Commission of Accreditation of Healthcare Organizations (JCAHO).

Conventionally, patients self-report their medication history to healthcare service providers. Self-reporting is typically accomplished via in-take forms and/or a manual interview process conducted by employees of a healthcare service provider. Self-reporting may lead to inaccuracies in constructing a medication history for a patient as the patient may incorrectly report and/or omit one or more medications that he/she is currently taking or has taken in the past. These inaccuracies may lead to improper diagnosis of a patient's medical condition and/or to improper treatment of the patient. Accordingly, there is a need in the industry for systems and methods for capturing and providing patient medication history.

SUMMARY OF THE INVENTION

Example embodiments of the invention may provide for systems and methods for capturing patient medication history and providing the patient medication history to a healthcare service provider, such as, a hospital, doctor's office, clinician, etc.

According to an example embodiment of the invention, there is a method for providing medication history information for a patient. A request for medication history information of a patient may be received, and the request may include identification information for the patient. At least one memory may be accessed utilizing at least a portion of the identification information. The at least one memory may include information associated with pharmacy claims transactions that is stored in the at least one memory in near real time as the pharmacy claims transactions are processed. Information associated with the medication history of the patient may be obtained from the at least one memory and the medication history information may be communicated in response to the received request.

According to another example embodiment of the invention, there may be a system for providing medication history information. The system may include at least a medication history database and a medication history service provider. The medication history database may include information associated with pharmacy claims transactions, wherein the information associated with the pharmacy claims transactions is stored in the medication history database in near real time as the pharmacy claims transactions are processed by a switch provider that interconnects pharmacies and adjudicators of the pharmacy claims transactions. The medication history service provider may be operable to receive a request from a healthcare service provider far a medication history of a patient of the healthcare service provider, the request including identification information for the patient. The medication history service provider may further be operable to access the medication history database utilizing at least a portion of the identification information and to obtain information associated with the medication history of the patient from the medication history database. The medication history service provider may communicate the medication history information in response to the received request.

According to yet another example embodiment of the invention, there may be a method for providing patient medication history information. A plurality of pharmacy claims transactions may be switched between one or more pharmacies and one or more claims transactions adjudicators. Information associated with the plurality of switched pharmacy claims transactions may be stored in near real time as the pharmacy claims transactions are switched. A request for medication history information of a patient may be received, the request including identification information for the patient. At least a portion of the identification information may be utilized to access the stored information associated with the plurality of switched pharmacy claims transactions. At least a portion of the stored information may be communicated in response to the received request.

Other embodiments, aspects, features, and advantages of the invention will become apparent to those skilled in the art from the following detailed description, the accompanying drawings, and the appended claims.

BRIEF DESCRIPTION OF THE DRAWINGS

Reference will now be made to the accompanying drawings, which are not necessarily drawn to scale, and wherein:

FIG. 9 illustrates an example web page that facilitates the receipt of patient medication history requests, according to an example embodiment of the invention.

FIG. 10 illustrates an example web page for displaying the results of a patient medication history request, according to an example embodiment of the invention.

FIG. 11 illustrates an example web page for displaying detailed medication history information for a patient, according to an example embodiment of the invention.

FIG. 12 illustrates another example web page for receiving patient medication history requests, according to an example embodiment of the invention.

FIG. 13 illustrates an example web page for sorting patient medication history information, according to an example embodiment of the invention.

DETAILED DESCRIPTION

Figure 1:
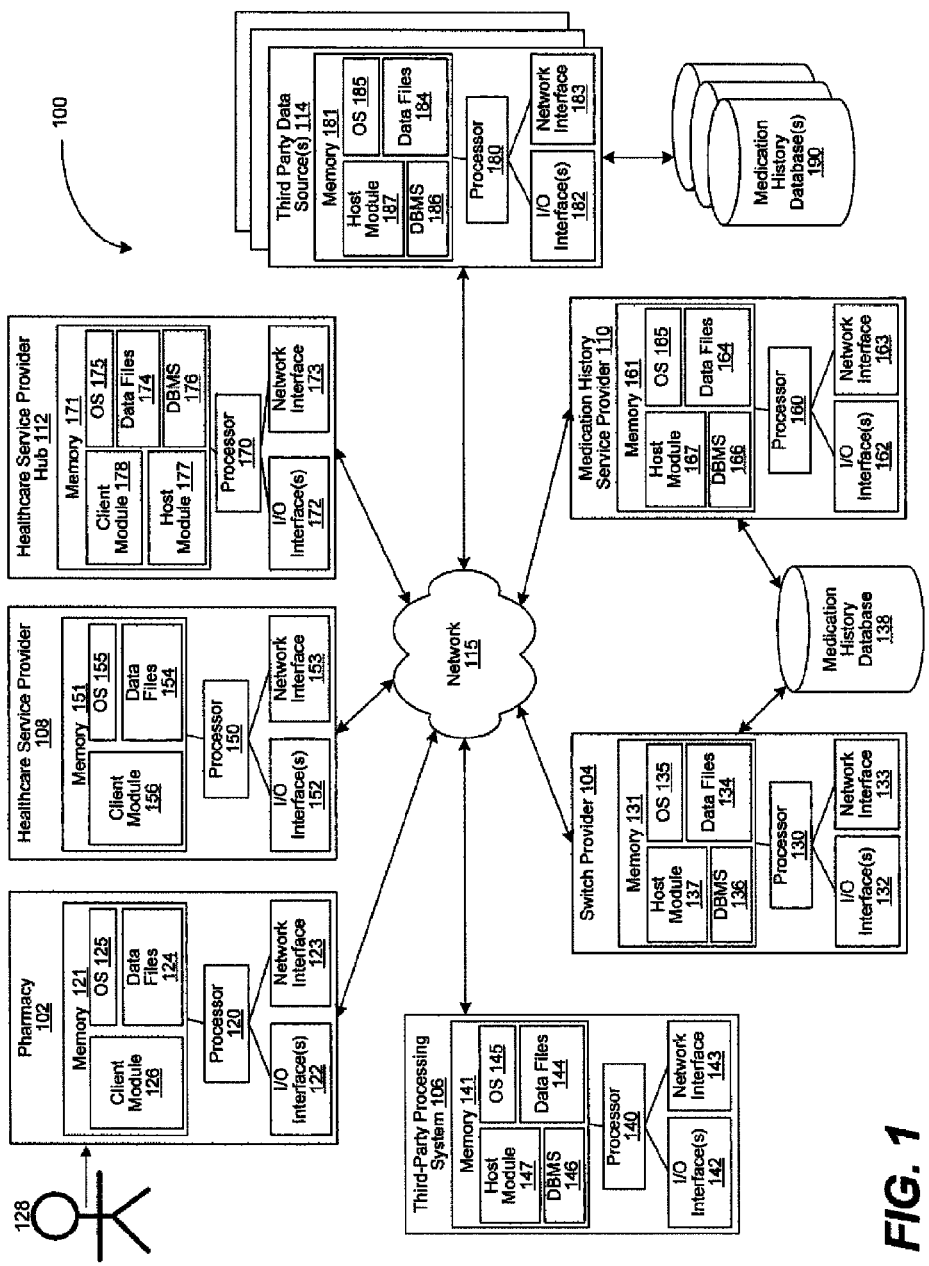
FIG. 1 shows a block diagram of a system for dynamically capturing, and providing, patient medication history, according to an example embodiment of the invention.

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The invention is described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

The terms "patient medication history," "medication history," "prescription history," and "patient prescription history," are used interchangeably throughout the description, and should be construed to cover the history of any prescription drugs, medications, medical treatments, and/or medical devices that may be obtained at a pharmacy, doctor's office, hospital or similar location using a prescription.

In accordance with example embodiments of the invention, a healthcare service provider, such as, a hospital, doctor's office, clinician, etc., may be provided with patient medication history. The patient medication history may be provided in response to a request received from the healthcare service provider, wherein the request includes patient identification information. The patient medication history may be provided to the healthcare service provider by a medication history service provider that retrieves the medication history from one or more medication history databases. Patient medication history information may be stored in the one or more medication history databases during the processing of pharmacy claims transactions. Additionally, the medication history service provider may retrieve medication history information from one or more third party data sources.

An example system in accordance with an embodiment of the invention is shown in FIG. 1, which shows a block diagram of a system 100 for dynamically capturing, and providing, patient medication history. In particular, the system 100 of FIG. 1 may include at least one pharmacy 102, at least one switch provider 104, at least one third-party processing system 106, at least one healthcare service provider 108, and at least one medication history service provider 110, which are each configured for accessing and reading associated computer-readable media having stored thereon data and/or computer-executable instructions for implementing the various methods of the invention. Additionally, certain embodiments of the invention may include at least one healthcare service provider hub or aggregator 112 and/or at least one third party data source 114. Generally, network devices and systems, including the one or more pharmacies 102, switch providers 104, third-party processing systems 106, medication history service providers 108, healthcare service provider hubs 112 and third party data sources 114 may have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy 102, switch provider 104, third-party processing system 106, and medication history service provider 110 may be in communication with each other via a network 115, which as described below can include one or more private and public networks, including the Internet. Each component of the system 100 may be in direct communication with one or more other components of the system 100 as desired in various embodiments of the invention. Additionally, in certain embodiments, a healthcare service provider hub 112 and/or one or more third party data sources 114 may be in communication with one or more other components of the system 100 via the network 115. Each of these components—the pharmacy 102, the switch provider 104, the third-party processing system 106, the healthcare service provider 112, the third party data sources 114, and the network 115—will now be discussed in turn.

First, the pharmacy 102 may be any processor-driven device, such as a personal computer, laptop computer, handheld computer, and the like. In addition to having a processor 120, the pharmacy 102 may further include a memory 121, input/output ("I/O") interface(s) 122 and a network interface 123. The memory 121 may store data files 124 and various program modules, such as an operating system ("OS") 125 and a client module 126. The client module 126 may be an Internet browser or other software, including a dedicated program, for interacting with the switch provider 104. For example, a user 128, such as a consumer, pharmacist, or other pharmacy employee, may utilize the client module 126 in preparing and providing prescription claims transaction requests, such as, prescription drug requests or orders, to the switch provider 104 for processing. The pharmacy 102 may also utilize the client module 126 to retrieve or otherwise receive data from the switch provider 104, including indications that one or more prescription claims transaction requests have been communicated to, received by, processed by, and or approved by a third-party processing system 106.

Still referring to the pharmacy 102, the I/O interface(s) 122 may facilitate communication between the processor 120 and various I/O devices, such as a keyboard, mouse, printer, microphone, speaker, monitor, bar code readers/scanners, RFID readers, and the like. The network interface 123 may take any of a number of forms, such as a network interface card, a modem, a wireless network card, and the like. These and other components of the pharmacy 102 will be apparent to those of ordinary skill in the art and are therefore not discussed in more detail herein. Additionally, the pharmacy 102 may be associated with any entity that fills or fulfills prescription requests for a patient, such as, a pharmacy, hospital pharmacy, etc.

The switch provider 104 may include any processor-driven device that is configured for receiving, processing, and/or fulfilling requests received from the pharmacy 102 related to pharmacy, benefits, prescription and/or medical claims transactions. For example, the switch provider 104 may include a claims transactions switch or network operated by RelayHealth™. The switch provider 104 may therefore include a processor 130, a memory 131, input/output ("I/O") interface(s) 132, and a network interface 133. The memory 131 may store data files 134 and various program modules, such as an operating system ("OS") 135, a database management system ("DBMS") 136, and a host module 137. The host module 137 may receive, process, and respond to requests from the respective client module 126 of the pharmacy 102, and may further receive, process, and respond to requests and/or communications from the respective host modules 146 of the third-party processing system 106. For example, the host module 137 may receive a prescription claims transaction request from a pharmacy 102, and the switch provider 104 may process the request and communicate the request to a third-party processing system 106 for adjudication. Following the adjudication of the claim by the third-party processing system 106, the switch provider 104 may receive an indication of either a successful or unsuccessful adjudication from the third-party processing system 106, and the switch provider 104 may communicate the indication to the pharmacy 102. Additionally, the switch provider 104 may store information associated with requested and/or adjudicated prescription claims transactions in one or more suitable memory devices and/or data repositories, such as, a medication history database 138.

According to an aspect of the invention, one or more suitable memory devices, such as, medication history database 138, may be associated with the switch provider 104. The switch provider 104 may store information associated with pharmacy claims transactions in the medication history database 138. A wide variety of different information may be stored in the medication history database 138 as desired in various embodiments of the invention. Information that may be stored includes, but is not limited to, identification information for a patient that is filling a subscription or obtaining prescribed medical equipment at the pharmacy 102 (e.g., name, address, zip code, date of birth, gender, etc.), insurance information associated with the patient (e.g., primary insurance provider, secondary insurance provider, insurance account numbers, co-pay amount, etc.), information associated with the prescribed drugs and/or medical equipment (e.g., an identification of the drug such as a National Drug Code (NDS), drug name, drug manufacturer, prescription amount, expiration date, price of the drug, etc.), information associated with the payment method utilized by the patient (e.g., cash, credit, check, etc.), information associated with the pharmacy 102 (e.g., name of pharmacy, pharmacy identification number, address of pharmacy, name of pharmacists, etc.), the date and time of the claims transaction request, information associated with the third-party processing system 106 (e.g., a Banking Identification (BIN)/Processor Control Number (PCN) for identifying a third-party processing system 106 as a destination of a claim request, a name of the third-party processing system, etc.), and/or information associated with the adjudication of the claim by a third-party service provider 106 (e.g., status of the claim adjudication, whether the claim was paid, amount paid, date paid, etc.). Additionally, the medication history database 138 may be utilized to store information associated with a wide variety of different types of pharmacy claims transactions, including but not limited to, insurance claims transactions, credit card transactions, check transactions, and/or cash transactions.

The third-party processing system 106 may include any processor-driven device that is configured for receiving, processing, and fulfilling requests from the pharmacy 102 or switch provider 104 related to pharmacy, benefits, prescription and/or medical claims transactions. The third-party processing system 106 may include a processor 140, a memory 141, input/output ("I/O") interface(s) 142, and a network interface 143. The memory 141 may store data files 144 and various program modules, such as an operating system ("OS") 145, a database management system ("DBMS") 146, and a host module 147. The host module 147 receives, processes, and responds to requests from the client module 126 of pharmacy 102, and further receives, processes, and responds to requests from the host module 137 of the switch provider 104. Those of ordinary skill in the art will appreciate that the third-party processing system 106 may include alternate and/or additional components, hardware or software. Additionally, the third-party processing system 106 may be associated with a payer of pharmacy benefits, such as, an insurance carrier, a health plan provider, a pharmacy benefits manager (PBM), a large employer group, etc.

According to an aspect of the invention, information associated with pharmacy claims transactions that are routed through the switch provider 104 is stored in the medication history database 138. The information may be stored at a wide variety of different times as desired in various embodiments of the invention. According to one embodiment of the invention, information associated with the transaction may be stored in a local memory associated with the switch provider 104 (e.g., a cache, a random access memory (RAM), etc.) as it is routed to the third-party processing system 106. The information may then be written to the medication history database 138 from the local memory. Information may be written from the local memory to the medication history database 138 at predetermined time intervals as desired in various embodiments of the invention, such as, once every minute, one every 15 minutes, once every hour, once every 2 hours, etc.). Alternatively, the information may be written to the medication history database 138 during the routing of the transaction to the third-party processing system 106. If the information is written to the medication history database 138 during the routing of a transaction or if the predetermined time interval for updating the medication history database 138 from local memory is relatively small, then the medication history database 138 may be updated regularly in near real time as claims transactions are processed by the switch provider 104.

In addition to processing and storing claims transaction requests received from a pharmacy 102 and routed to a third-party processing system 106, the switch provider 104 may also store information received from a third-party processing system 106 in the medication history database 138, such as, information associated with the adjudication of a pharmacy claim transaction. The switch provider 104 may store information received from a third-party processing system in a similar manner as that described above for storing information received from a pharmacy 102. In this regard, medication history information associated with patients may be stored. Medication history information may be stored for any number of patients whose pharmacy claims transactions are routed through the switch provider 104.

The healthcare service provider 108 may include any processor-driven device that is configured for requesting and receiving medication history information associated with a patient of the healthcare service provider 108. The healthcare service provider may include a processor 150, a memory 151, input/output ("I/O") interface(s) 152, and a network interface 153. The memory 151 may store data files 154 and various program modules, such as an operating system ("OS") 155, and a client module 156. The client module 156 may communicate one or more requests for patient medication history information, and the client module may receive patient medication history information in response to the requests. As described in greater detail below, the client module 156 may communicate requests directly to the medication history service provider 110 or the requests may be communicated through one or more other entities, such as, a healthcare service provider hub or aggregator 112. In certain embodiments of the invention, the client module 156 may be an Internet browser or other software, including a dedicated program, for interacting with the switch provider 104. In other embodiments of the invention, the client module 156 may be a software program that communicates transaction information containing patient identification information. The transaction information may be communicated directly to the medication history service provider 110 or, alternatively, to a healthcare service provider aggregator 112. The patient identification information may be extracted and utilized to identify medication history information associated with the patient. The patient identification information may be extracted by the medication history service provider 110 or by the healthcare service provider aggregator 112. If the healthcare service provider aggregator 112 extracts the patient identification information, then the healthcare service provider aggregator 112 may communicate a request for patient medication history information to the medication history service provider 110 on behalf of the healthcare service provider 108.

Still referring to the healthcare service provider 108, the I/O interface(s) 152 may facilitate communication between the processor 150 and various I/O devices, such as a keyboard, mouse, printer, microphone, speaker, monitor, bar code readers/scanners, RFID readers, and the like. In this regard, the I/O interface(s) may facilitate the collection of patient identification information that is utilized in patient medication history requests. The network interface 153 may take any of a number of forms, such as a network interface card, a modem, a wireless network card, and the like. These and other components of the healthcare service provider 108 will be apparent to those of ordinary skill in the art and are therefore not discussed in more detail herein.

Additionally, the healthcare service provider 108 may be associated with any healthcare service entity that desires patient medication history for diagnosis and/or treatment purposes, such as, a hospital, a doctor's office, a client, etc. Patient identification information may be gathered at the healthcare service provider 108 and used in the generation of a request for patient medication history information. For example, a hospital employee may utilize one or more I/O devices and the client module 156 to input patient identification information for the generation of a request for medication history information for the patient. The request may be communicated either directly or indirectly to the medication history service provider 110 and patient medication history information may be communicated to the healthcare service provider 108.

The medication history service provider 110 may include any processor-driven device that is configured for receiving and processing requests for patient medication history. For example, the medication history service provider 110 may include a medication history service provider 110 operated by RelayHealth™. The medication history service provider 110 may therefore include a processor 160, a memory 161, input/output ("I/O") interface(s) 162, and a network interface 163. The memory 161 may store data files 164 and various program modules, such as an operating system ("OS") 165, a database management system ("DBMS") 166, and a host module 167. The host module 167 may receive, process, and respond to requests for patient medication history. During the processing of requests, the medication history service provider 110 may access the medication history database 138 and one or more third party data sources 114 in order to gather patient medication history information, as explained in greater detail below.

Patient medication history requests may be received from the respective client module 156 of the healthcare service provider 108 either directly or via one or more other components of the system 100, such as, via a healthcare service provider hub 112. A request for patient medication history may include identification information for one or more patients. The medication history service provider 110 may utilize at least a portion of the identification information to search the medication history database 138. Additionally, in certain embodiments of the invention, the medication history service provider 110 may utilize at least a portion of the identification information to communicate requests for patient medication history information to one or more third party data sources 114. Patient medication history information may be received from the one or more third party data sources 114 in response to the requests. Additionally, patient medication history information received from one or more third party data sources 114 may be combined or aggregated with patient medication history information retrieved from the medication history database 138.

Although the medication history service provider 110 is illustrated in FIG. 1 as a separate component of the system 100, the medication history service provider 110 may be combined with the switch provider 104 in certain embodiments of the invention.

The healthcare service provider hub or aggregator 112 may include any processor-driven device that is configured for routing patient medication history requests from a healthcare service provider 108 to the medication history service provider 110. For example, the healthcare service provider hub or aggregator may be a hospital aggregator that provides transactions processing and/or other services to one or more hospitals or other healthcare service providers. As another example, the healthcare service provider hub or aggregator may be a hospital vendor that provides software and/or services to one or more hospitals or other healthcare service providers.

The healthcare service provider hub may include a processor 170, a memory 171, input/output ("I/O") interface(s) 172, and a network interface 173. The memory 171 may store data files 174 and various program modules, such as an operating system ("OS") 175, a DBMS 176, a host module 177, and a client module 178. The host module 177 may receive requests for patient medication history information from the client module 156 of the healthcare service provider 108, and the client host module 177 may process the requests. The client module 178 may transmit requests received from the healthcare service provider 108 to the host module 167 of the medication history service provider 110. In this regard, healthcare service provider requests for patient medication history may be routed to the medication history service provider 110 by the healthcare service provider hub 112.

The third party data source(s) 114 may include any number of processor-driven devices that are configured to receive and process requests for patient medication history information. In one embodiment of the invention, each of the third party data sources 114 may receive requests for patient medication history information from the medication history service provider 110, and each of the third party data sources may process the requests and communicate patient medication history information to the medication history service provider 110. Additionally, in various embodiments of the invention, requests may be received from other components of the system 100 and processed by the third party data source(s) 114.

A wide variety of different entities may function as third party data source(s) 114, such as, prescription benefit managers, pharmacy benefit managers, insurance companies, healthcare coverage companies, etc. For example, Caremark™, ESI™, and Netco™ may be prescription benefit managers that function as third party data sources 114. As another example, various Blue Cross Blue Shield Association™ companies and/or other healthcare coverage companies may function as third party data sources.

Each of the third party data sources 114 may include a processor 180, a memory 181, input/output ("I/O") interface(s) 182, and a network interface 183. The memory 181 may store data files 184 and various program modules, such as an operating system ("OS") 185, a DBMS 186, and a host module 187. The host module 187 may receive and process requests for patient medication history information. Each of the third party data sources 114 may utilize information included in a request, such as, patient identification information, to access one or more suitable memory devices and/or data repositories, such as, an associated medication history database 190. Patient medication history information may then be communicated to a requesting entity by a third party data source 114. In one embodiment, requests for patient medication history information may be received from the medication history service provider 110. In this regard, the medication history service provider 110 may supplement any information retrieved from the medication history database 138 associated with the medication history service provider 110. Requests for medication history information may be communicated from the medication history service provider 110 to the various third party data sources 114 during the processing of a request received from a healthcare service provider 108 or, alternatively, at predetermined time intervals, such as, once an hour, once a day, etc.

The medication history databases 190 associated with the various third party data sources 114 may include information associated with pharmacy claims transactions, pharmacy cash transactions, and/or other pharmacy transactions. The pharmacy claims transaction may be transactions that are processed by the third party data sources 114, switched or routed through the third party data sources 114, and/or adjudicated by the third party data sources 114.

The network 115 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 115 may also allow for real-time, off-line, and/or batch transactions to be communicated or transmitted between various components of the system 100, such as, between the pharmacy 102 and the switch provider 104. Due to network connectivity, various methodologies as described herein may be practiced in the context of distributed computing environments. For example, although the pharmacy 102 is shown for simplicity as being in communication with the switch provider 104 via one intervening network 115, it is to be understood that any other network configuration is possible. For example, intervening network 115 may include a plurality of networks, each with devices such as gateways and/or routers for providing connectivity between or among networks 115. Instead of or in addition to a network 115, dedicated communication links may be used to connect the various components or devices in accordance with example embodiments of the invention. For example, the switch provider 104 may form the basis of network 115 that interconnects the pharmacy 102 and the third-party processing system 108.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
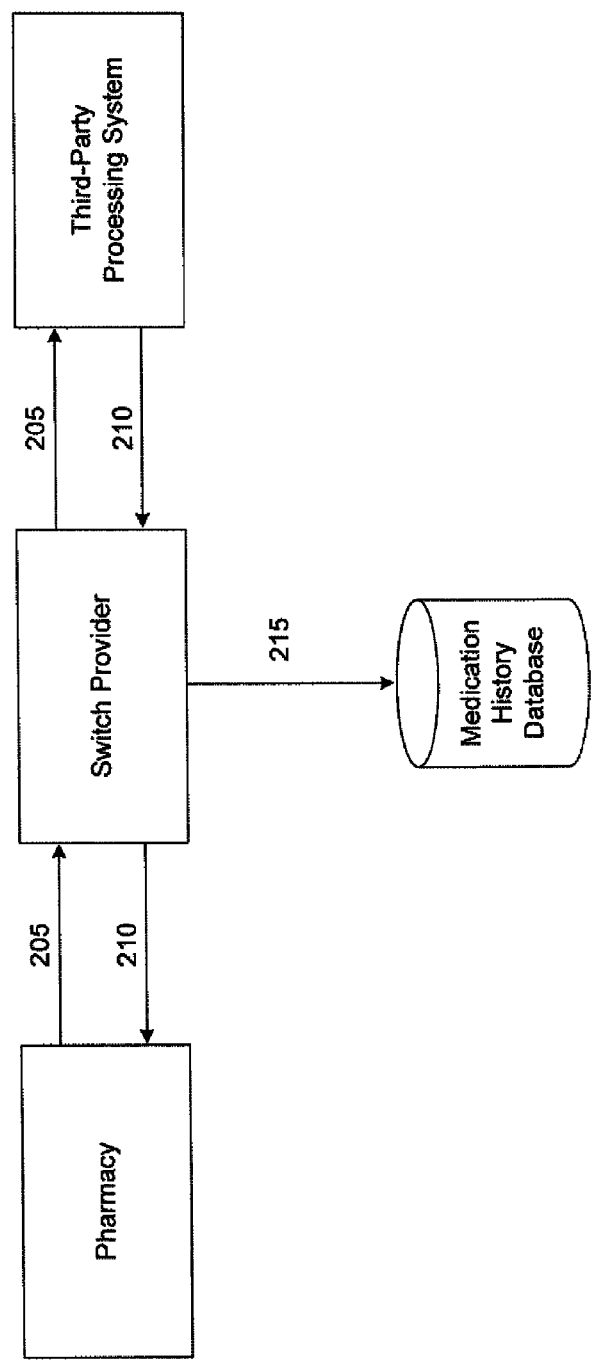
FIG. 2 illustrates an example block diagram for capturing pharmacy claims, according to an example embodiment of the invention.

FIG. 2 illustrates an example block diagram for capturing pharmacy claims, according to an example embodiment of the invention. A pharmacy, such as pharmacy 102 shown in FIG. 1, may transmit a claim request 205 on behalf of a customer to a switch provider, such as switch provider 104 shown in FIG. 1. The claim request 205 may include a wide variety of different information associated with a pharmacy claim as desired in various embodiments of the invention. The switch provider 104 may receive the claim request 205 and route the claim request 205 to an appropriate third-party processing system, such as third-part processing system 106, for further processing and/or adjudication. According to an example embodiment, the switch provider 104 may utilize a BIN/PCN in the received claim request 205 to determine the appropriate third-party processing system 106 to route the claim request 205 to. The switch provider 104 may also include a routing table, perhaps stored in memory, such as memory 131, for determining which third-party payor 106 to route the claim request 205 to. According to an example embodiment of the invention, the third-party processing system 106 may be any pharmacy claims processing system such as a pharmacy benefits manager (e.g., a pharmacy benefits manager (PBM)), an insurance company, or a government payor (e.g., Medicare, Medicaid). Alternatively, the third-party processing system 106 may be a discount program processing system, including a discount program where a customer is responsible for paying for a portion or entire cost of the drug.

The third-party processing system 106 may receive and adjudicate the claim request 205. In particular, the third-party processing system 106 may determine benefits coverage for the received claim request 205 according to an adjudication process associated with eligibility, pricing, and/or utilization review. According to an example embodiment of the invention, the adjudication process may include determining a covered amount such as an insured amount, as well as a customer amount such as a co-pay amount. The third-party processing system 106 may transmit an adjudicated claim 210 to the switch provider 104. If the drug is covered, at least in part, by the third-party processing system 106, then the adjudicated claim 210 may include the covered amount, and the customer amount. On the other hand, if the drug is not covered by the payor 106, then the adjudicated claim 210 may include a rejected claim notice indicating that the drug is not covered by the third-party processing system 106. The adjudicated claim 210 may also include some or all of the information included in the claim request 205, discussed herein. The switch provider 104 receives the adjudicated claim 210 from the third-party processing system 106 and then routes the adjudicated claim 210 back to the pharmacy 102. At the pharmacy 102, the patient will then be responsible for any customer amount (e.g., co-pay amount) indicated by the adjudicated claim 210.

In addition to routing the claim request 205 and the adjudicated claim 210, the switch provider 104 may also capture and/or store information associated with the claim request 205 and/or the adjudicated claim. The information may be stored in one or more records 215 in a suitable memory device or data repository associated with the switch provider 104, such as, in medication history database 138 shown in FIG. 1. In various embodiments of the invention, any number of records 215 may be stored in the medication history database 138. Additionally, each record 215 may include a wide variety of information as desired in various embodiments of the invention, including but not limited to, the information discussed above with reference to FIG. 1. In this regard, information associated with pharmacy claims transactions may be stored by a switch provider 104 that routes the claims. In certain embodiments of the invention, the information may be stored in near real time or approximately in real time as the claims are routed by the switch provider 104.

Figure 3:
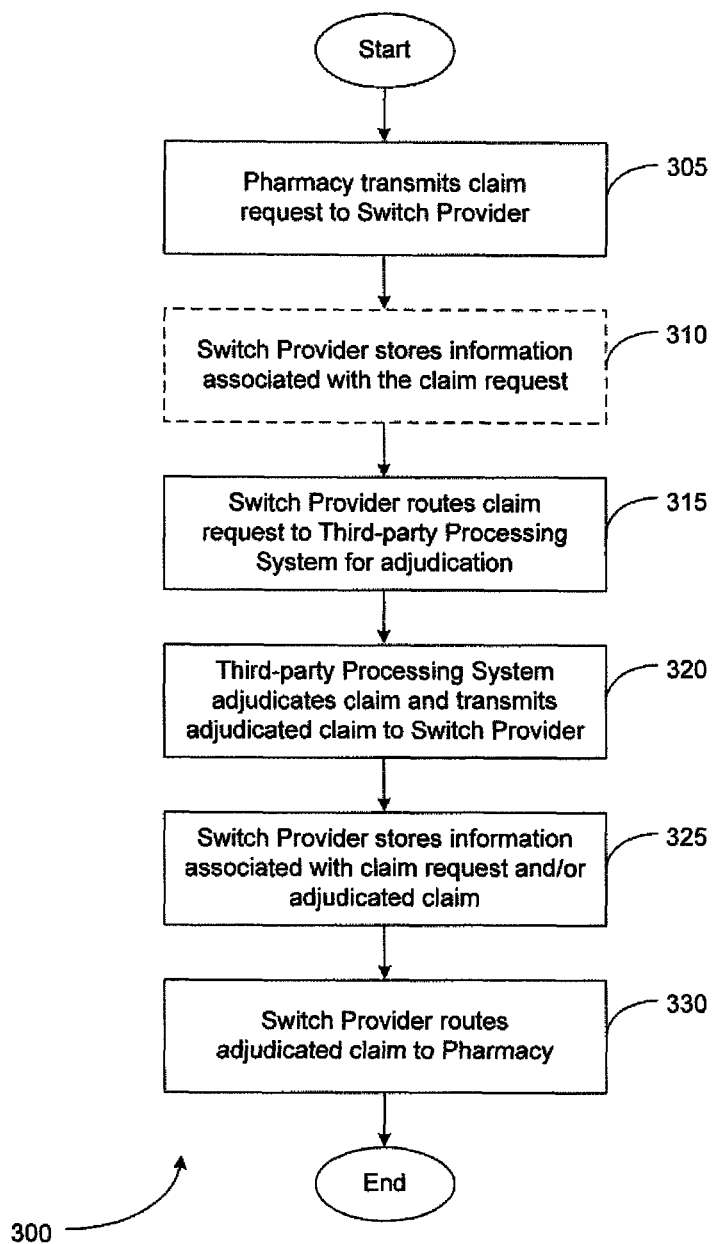
FIG. 3 illustrates an example flow diagram of a method for capturing pharmacy claims, according to an example embodiment of the invention.

FIG. 3 illustrates an example flow diagram of a method 300 for capturing pharmacy claims, according to an example embodiment of the invention. The method 300 may begin at block 305. At block 305, a pharmacy, such as pharmacy 102, may transmit a claim request, such as claim request 205, to a switch provider, such as switch provider 104. At block 310, which may be optional in some embodiments of the invention, the switch provider 104 may store information associated with the received claim request 205 in one or more suitable memories or data repositories, such as, medication history database 138. Information associated with the claim request 205 may be stored in the medication history database 138 in near real time or approximately in real time as the claim request 205 is processed by the switch provider 104. Alternatively, information associated with the claim request 205 may be stored in one or more local memories (e.g., a cache or a random access memory) associated with the switch provider 104 during the processing of the claim request 205, and the information may later be written to the medication history database 138. The information may be written to the medication history database 138 from the one or more local memories in near real time, following the adjudication of the claim, and/or at a predetermined time interval, such as, once every minute, once every 15 minutes, once every hour, etc.

At block 315, the switch provider 104 may route the claim request 205 to a third-party processing system, such as third-party processing system 106, for adjudication. At block 320, the claim request 205 may be adjudicated by the third-party processing system 106 and an adjudicated claim, such as adjudicated claim 210, may be transmitted or otherwise communicated to the switch provider 104 by the third-party processing system 106.

At block 325, the switch provider 104 may store information associated with the claim request 205 and/or the adjudicated claim 210 in one or more suitable memories or data repositories, such as, medication history database 138. Information associated with the claim request 205 and/or the adjudicated claim 210 may be stored in the medication history database 138 in near real time or approximately in real time as the adjudicated claim 210 is processed by the switch provider 104. Alternatively, information associated with the claim request 205 and/or adjudicated claim 210 may be stored in one or more local memories (e.g., a cache or a random access memory) associated with the switch provider 104 during the processing of the claim request 205 and/or the adjudicated claim 210, and the information may later be written to the medication history database 138. The information may be written to the medication history database 138 from the one or more local memories in near real time, following the adjudication of the claim, and/or at a predetermined time interval, such as, once every minute, once every 15 minutes, once every hour, etc. In this regard, information associated with claim requests and/or adjudicated claims that are processed by the switch provider 104 may be stored in the medication history database 138 for subsequent retrieval in the processing of requests for patient medication history.

At block 330, the switch provider 104 may route the adjudicated claim 210 to the pharmacy 102. The method 300 may end following block 330.

The operations described in the method 300 of FIG. 3 do not necessarily have to be performed in the order set forth in FIG. 3, but instead may be performed in any suitable order. For example, in certain embodiments of the invention, the switch provider 104 may store information associated with a claim request 205 and/or an adjudicated claim 210 in the medication history database 138 following the routing of the adjudicated claim 210 to the pharmacy 102. Additionally, various operations described in the method 300 of FIG. 3 may be performed in a parallel manner. Additionally, in certain embodiments of the invention, more or less than all of the operations set forth in FIG. 3 may be performed.

Figure 4:
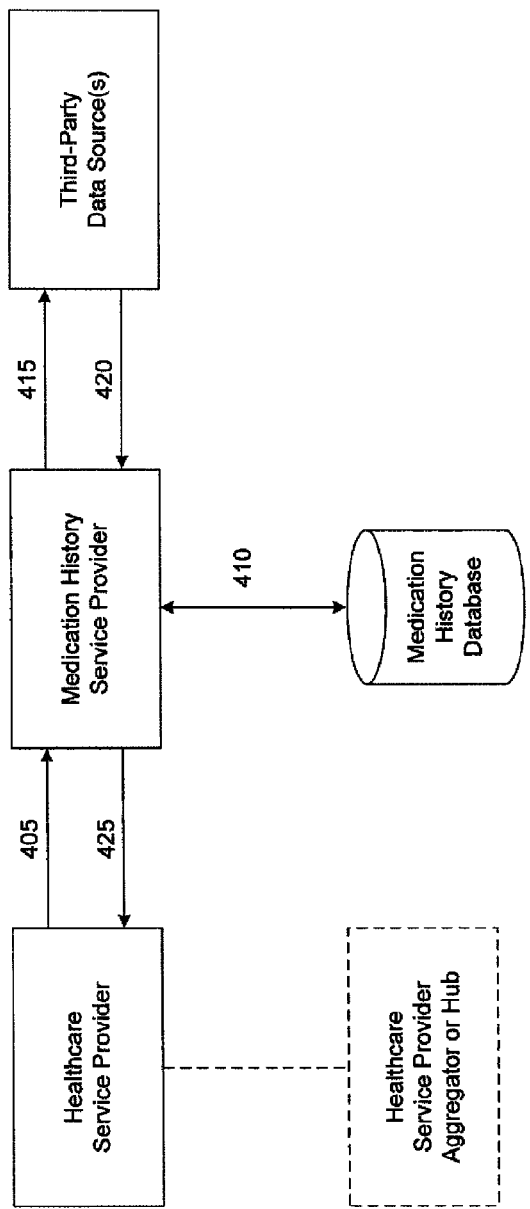
FIG. 4 illustrates an example block diagram for providing patient medication history, according to an example embodiment of the invention.

FIG. 4 illustrates an example block diagram for providing patient medication history, according to an example embodiment of the invention. A healthcare service provider, such as healthcare service provider 108, may communicate a request 405 for patient medication history to a medication history service provider, such as medication history service provider 110. In some embodiments of the invention, the request 405 may be communicated directly to the medication history service provider 110 by the healthcare service provider 108. As explained in greater detail below, the request 405 may be communicated to the medication history service provider 110 via a suitable web portal or other Internet based application. Alternatively, the request 405 may be communicated to the medication history service provider 110 by patient management software, prescription drug software, or other applications operated by the healthcare service provider 108. For example, the request 405 may be communicated to the medication history service provider 110 by patient intake and/or management software utilized by the healthcare service provider. An appropriate transaction set, such as, a National Council for Prescription Drug Programs (NCPDP) transaction set, may be embedded in the software utilized by the healthcare service provider 108, and the transaction set may facilitate the communication of the request 405. The software may be provided to the healthcare service provider 108 by one or more vendors that operate as healthcare service provider aggregators or hubs, such as healthcare service provider hub 112. Accordingly, in certain embodiments of the invention, the software may be branded as software of the one or more vendors. In such a situation, the software may operate to send the request 405 directly to the medication history service provider 110. Alternatively, the software may send requests to the healthcare service provider hub 112 for routing to the medication history service provider 110, as discussed in greater detail below with reference to FIG. 5.

The medication history service provider 110 may receive the request 405 and process the request 405 in order to obtain patient medication history information. The request 405 may include identification information for one or more patients, for example, names of the patients, zip codes of the patients, addresses of the patients, dates of birth for the patients, genders for the patients, insurance information for the patients, driver's license numbers of patients, social security numbers of patients, other identifying numbers for patients, information concerning whether the patients have consented to their medication history information being accessed, etc. The medication history service provider 110 may utilize at least a portion of the identification information to obtain patient medication history information from various sources, including from a medication history database, such as medication history database 138 and/or from one or more third party data sources, such as data sources 114. Additionally, the request 405 may include one or more dates, times, ranges of dates, and/or ranges of times for which patient medication history is sought. These dates and/or times may be utilized to filter patient medication history information. For example, patient medication history may be requested for the previous month.

According to an aspect of the invention, the medication history service provider 110 may access the medication history database 138 to obtain stored patient medication history information 410. In this regard, the medication history service provider 110 may obtain medication history information associated with pharmacy claims transactions that have been processed by an associated switch network, such as switch network 104. In certain embodiments of the invention, claims transactions may be processed by the switch provider 104 and stored in the medication history database 138 in near real time. In this situation, the medication history service provider 110 may have access to the stored information about the processed claims transactions in near real time. Thus, the patient medication history information 410 obtained by the medication history service provider 110 may be relatively current and up-to-date. For example, an individual may have a prescription filled at a pharmacy in the morning, and the individual may be admitted to a hospital later that day. The hospital may request medication history information from the medication history service provider 110, and the medication history database 138 may be accessed in processing the request. Information obtained from the medication history database 138 may include information concerning the filling of the prescription earlier in the same day. Thus, when medication history information is communicated to the requesting hospital, the information may be relatively current and up-to-date.

According to another aspect of the invention, the medication history service provider 110 may obtain medication history information from one or more third party data sources 114. In this regard, medication history information may be obtained for pharmacy claims transactions that are not processed by the switch provider 104, for example, pharmacy claims transactions processed by a separate switch provider and/or mail order pharmacy claims. Additional information for pharmacy claims transactions that are processed by the switch provider 104 may also be obtained from the one or more third party data sources 114. The medication history service provider 110 may communicate requests 415 for patient medication history information to one or more third party data sources 114. The requests may obtain identification information for one or more patients. The one or more third party data sources 114 may process the requests and obtain patient medication history information. For example, the one or more third party data sources 114 may utilize at least a portion of the patient identification information to access one or more memories or data repositories, such as medication history databases 190, in order to obtain stored medication history information. As another example, the one or more third party data sources 114 may send requests to additionally entities for the patient medication history information. Once patient medication history information is accessed and/or obtained by one or more third party data sources 114, the one or more third party data sources 114 may communicate replies 420 to the medication history service provider 110 that include at least a portion of the accessed or obtained patient medication history information. Alternatively, if no patient medication history information is found or obtained by a third party data source 114, a reply 420 may be communicated to the medication history service provider 110 indicating that no information was found.

A wide variety of different factors may be taken into consideration by a medication history service provider 110 in determining whether or not requests 415 for patient medication history information will be communicated to one or more third party data sources 114. These factors include, but are not limited to, a determination as to whether information is found in the associated medication history database 138, preferences of the requesting healthcare service provider 108, preferences associated with a healthcare service provider hub or aggregator 112, etc. For example, in certain embodiments of the invention, requests 415 may be communicated to one or more third party data sources 114 if it is determined that no patient medication history information is stored in the medication history database 138 associated with the medication history service provider 110 or that the stored information is incomplete. As another example, in certain embodiments, requests 415 may be communicated to one or more third party data sources 114 if the healthcare service provider 108 has indicated (either in prestored preferences or with a communicated request 405) that third party data sources 114 should be accessed. For example, a healthcare service provider 108 may indicate that all available data sources should be accessed, that specified data sources should be accessed, and/or that a certain number of available data sources should be accessed. Data sources that are accessed may also be prioritized in accordance with a wide variety of different factors, such as, costs associated with accessing the data sources, response time of the data sources, the frequency that the data sources are updated, the accuracy of the data sources, etc.

Additionally, in some embodiments of the invention, requests may be communicated to a plurality of third party data sources 114 in parallel. The requests may also be communicated to the third party data sources 114 in parallel with accessing the medication history database 138 associated with the medication history service provider 110. In some embodiments of the invention, requests may be communicated to the third party data sources 114 either before or after accessing the medication history database 138. Additionally, in some embodiments of the invention, one or more requests may be communicated to different third party data sources 114 in a non-parallel manner, such as, in a sequential manner.

Information received from the one or more third party data sources 114 may be reconciled with and/or aggregated with that obtained from the medication history database 138. Duplicative information may be deleted. Additionally, any information received from the one or more third party data sources 114 may be stored in the medication history database 138 and/or in one or more other data repositories associated with the medication history service provider 110.

The medication history service provider 110 may communicate a response 425 to the healthcare service provider 108 after accessing the medication history database 138 and/or receiving responses 420 from the one or more data sources 114. The response 425 communicated to the healthcare service provider 108 may contain a portion or all of the medication history information for the patient(s) that was obtained by the medication history service provider 108. Alternatively, if no patient medication history information was obtained by the medication history service provider 110, the response 425 may indicate that no patient medication history information was found.

Figure 5:
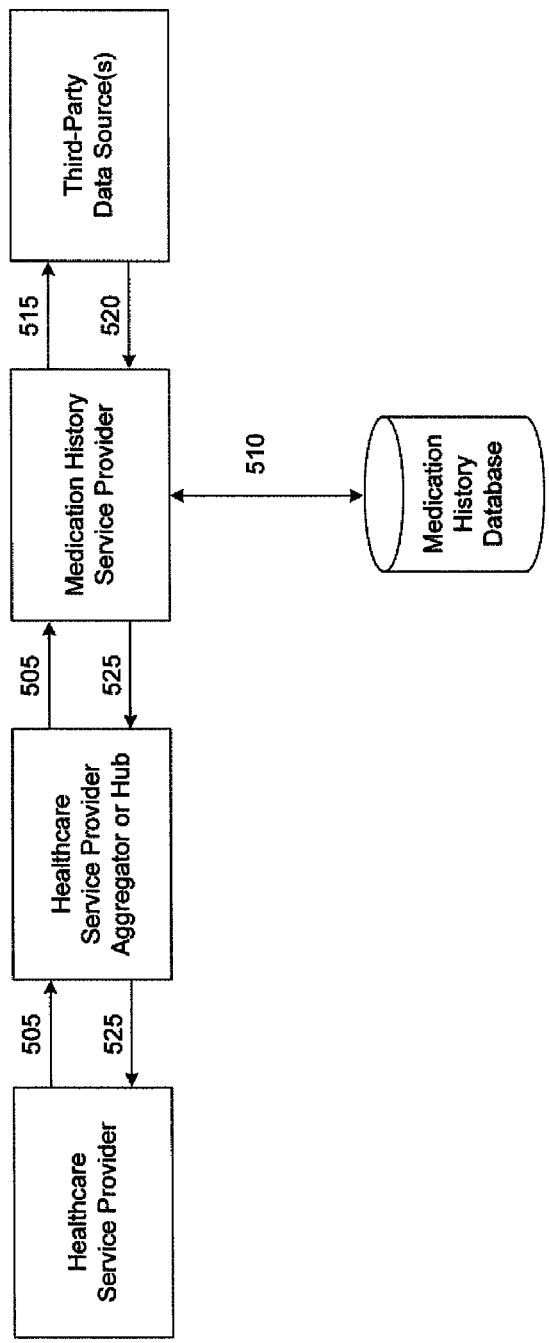
FIG. 5 illustrates an example block diagram for providing patient medication history, according to another example embodiment of the invention.

FIG. 5 illustrates an example block diagram for providing patient medication history, according to another example embodiment of the invention. The diagram illustrated in FIG. 5 may be similar to that shown in FIG. 4 with the exception of further including a healthcare service provider aggregator or hub, such as hub 112, that routes communications between a healthcare service provider, such as healthcare service provider 108, and a medication history service provider, such as medication history service provider 110.

With reference to FIG. 5, a healthcare service provider 108 may communicate a request 505 for patient medication history to a healthcare service provider aggregator 112, and the healthcare service provider aggregator 112 may route or otherwise communicate the request 505 to the medication history service provider 110. In some embodiments of the invention, as explained in greater detail below, the request 505 may be communicated to the healthcare service provider aggregator 112 via a suitable web portal or other Internet based application. Alternatively, in certain embodiments, the request 505 may be communicated to the healthcare service provider aggregator 112 by patient management software, prescription drug software, or other applications operated by the healthcare service provider 108, as described above with reference to FIG. 4.

The medication history service provider 110 may receive the request 505 and process the request 505 in order to obtain patient medication history information. The request 505 may include identification information for one or more patients, for example, names of the patients, zip codes of the patients, addresses of the patients, dates of birth for the patients, genders for the patients, insurance information for the patients, information concerning whether the patients have consented to their medication history information being accessed, desired dates, desired times, desired ranges of dates, desired ranges of times, etc. The medication history service provider 110 may utilize at least a portion of the identification information to obtain patient medication history information from various sources including from a medication history database, such as medication history database 138 and/or from one or more third party data sources, such as data sources 114. The process for obtaining information from a medication history database 138 and/or from one or more third party data sources may be similar to that described above with reference to FIG. 4. In short, medication history information 510 may be obtained by accessing the medication history database 138. Additionally, requests 515 for medication history information may be communicated to one or more third party data sources 114, and responses 520 including the requested information may be received from the one or more third party data sources. The medication history service provider 110 may communicate a response 525 to the healthcare service provider aggregator 112 after accessing the medication history database 138 and/or receiving responses 520 from the one or more data sources 114. The response 525 communicated to the healthcare service provider aggregator 112 may contain a portion or all of the medication history information for the patient(s) that was obtained by the medication history service provider 108. Alternatively, if no patient medication history information was obtained by the medication history service provider 110, the response 525 may indicate that no patient medication history information was found. The healthcare service provider aggregator 112 may route or otherwise communicate the response 525 to the healthcare service provider 108.

The example block diagrams and data flows illustrated in FIGS. 4 and 5 are provided by way of example only to aid in understanding the invention. It will be appreciated that different data flows for retrieving patient medication history information may be utilized in accordance with various embodiments of the invention. For example, in one embodiment, a healthcare service provider may request patient medication history information from both a medication history service provider and from one or more third party data sources using one or more appropriate software programs. These requests may be communicated directly from the healthcare service provider or routed through a healthcare service provider aggregator or hub. As another example, requests for patient medication history information may be made by a healthcare service provider aggregator or hub to the medication history service provider and/or to one or more third party data sources. Received information may then be communicated to a healthcare service provider. As yet another example, the medication history service provider may periodically requests patient medication history information from one or more third party data sources, and any received information may be reconciled with and stored in a local medication history database. Upon receipt of a request for patient medication history information, the medication history service provider may simply access the medication history database that contains the aggregated information. Indeed, many different network connections and/or data flows may be utilized as desired in various embodiments of the invention.

Figure 6:
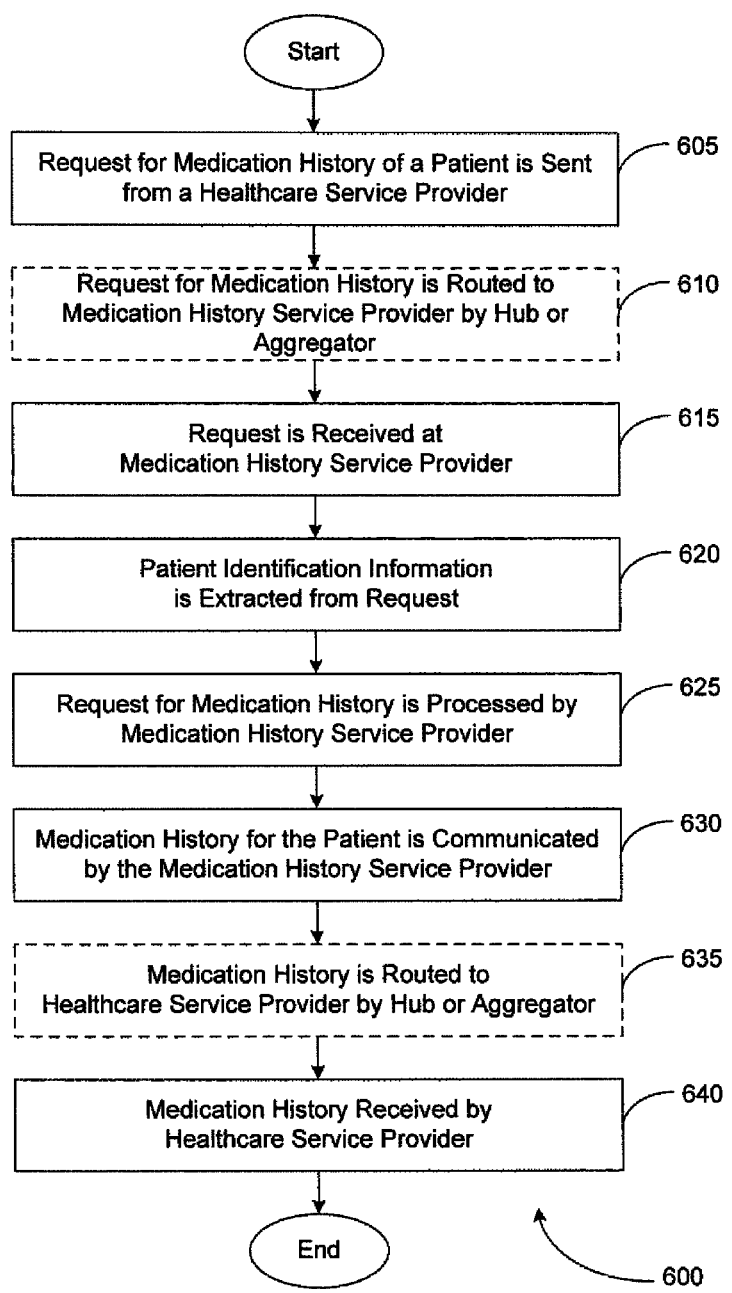
FIG. 6 illustrates an example flow diagram of a method for providing patient medication history, according to an example embodiment of the invention.

FIG. 6 illustrates an example flow diagram of a method 600 for providing patient medication history, according to an example embodiment of the invention. The method 600 may be utilized to receive and process requests for patient medication history that are made by patient management software, prescription drug software, or other applications operated by a healthcare service provider, such as healthcare service provider 108. These requests may or may not be routed through a healthcare service provider hub or aggregator, such as aggregator 112.

The method 600 may begin at block 605. At block 605, a request for medication history information for a patient may be communicated from a healthcare service provider 605. The request may be communicated directly to a medication history service provider, such as medication history service provider 110. Alternatively, the request may be communicated to a service provider hub or aggregator 112 and routed to the medication history service provider 110, as illustrated in optional block 610. The request may include identification information for one or more patients for whom medication history information is sought. Patient identification information may include, but is not limited to, names of the patients, zip codes of the patients, addresses of the patients, dates of birth for the patients, genders for the patients, insurance information for the patients, and/or information concerning whether the patients have consented to their medication history information being accessed.

At block 615, the request for medication history information may be received at the medication history service provider 110. The patient identification information for the one or more patients may be extracted from the request at block 620, and the request for medication history information may be processed by the medication history service provider at block 625. The patient identification information may be utilized in the processing of the request. One example method for processing the request is described in greater detail below with reference to FIG. 7.

Following the processing of the request at block 625, medication history information for the one or more patients may be communicated by the medication history service provider at block 630. In some embodiments of the invention, the medication history information may be communicated directly to the requesting healthcare service provider 108. Alternatively, in some embodiments of invention, the medication history information may be communicated to a service provider hub or aggregator 112 and routed to the healthcare service provider 108, as illustrated in optional block 635. The medication history information may be received by the requesting healthcare service provider at block 640. The method 600 may end following block 640.

The operations described in the method 600 of FIG. 6 do not necessarily have to be performed in the order set forth in FIG. 6, but instead may be performed in any suitable order. Additionally, in certain embodiments of the invention, more or less than all of the operations set forth in FIG. 6 may be performed.

Figure 7:
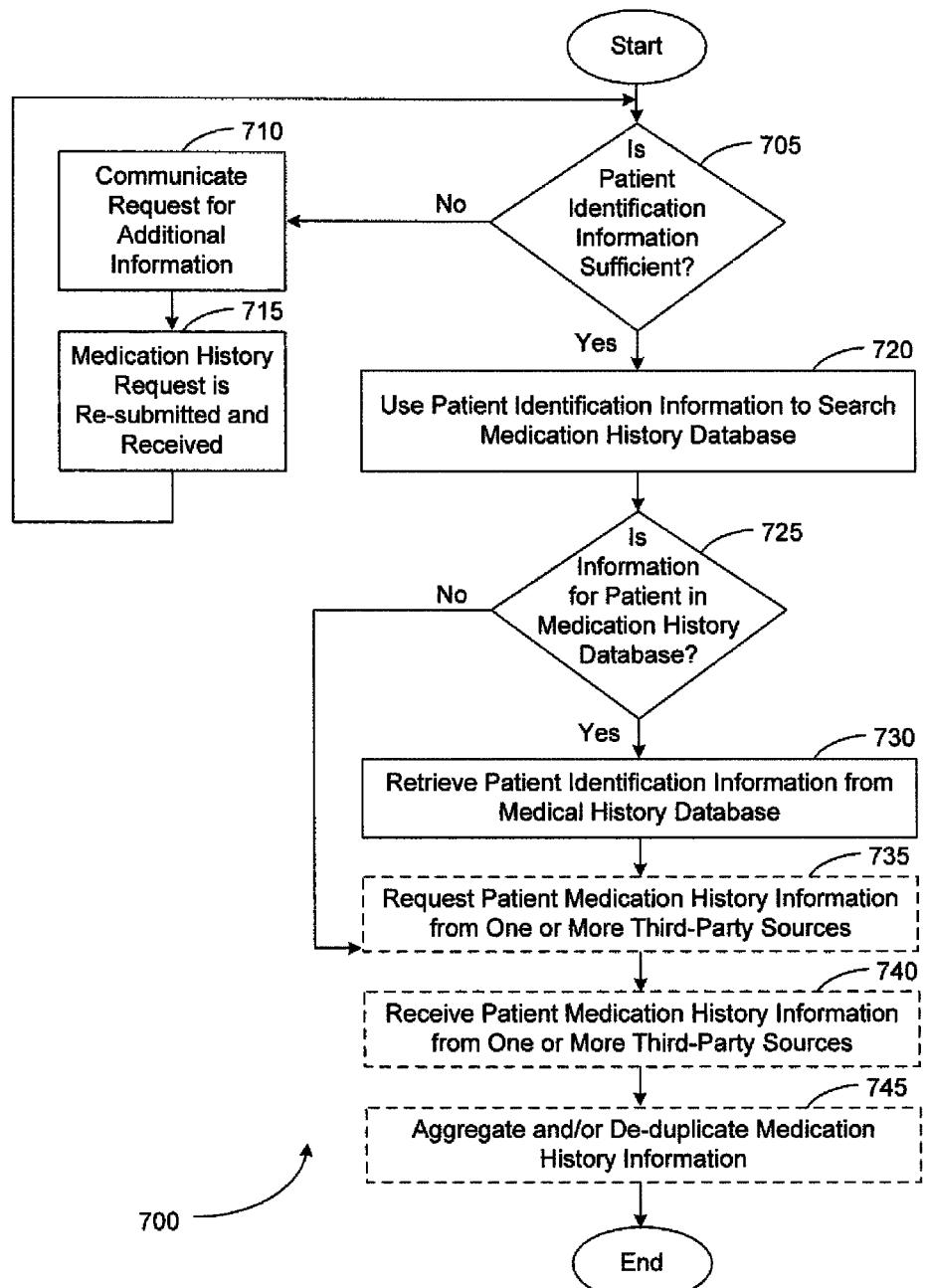
FIG. 7 illustrates an example flow diagram of a method for accessing and/or obtaining patient medication history information, according to an example embodiment of the invention.

FIG. 7 illustrates an example flow diagram of a method 700 for accessing and/or obtaining patient medication history information, according to an example embodiment of the invention. The method 700 shown in FIG. 7 may be utilized to process a request for patient medication history information. During the processing of the request, patient medication history information may be obtained from a patient medication history database, such as database 138, and/or from one or more third party data sources, such as third party data sources 114.

The method 700 may begin at block 705. A block 705, a determination may be made as to whether patient identification information included in a received request is sufficient to access and/or obtain patient medication history information. Patient identification information may include, but is not limited to, names of the patients, zip codes of the patients, addresses of the patients, dates of birth for the patients, genders for the patients, insurance information for the patients, and/or information concerning whether the patients have consented to their medication history information being accessed. A minimum amount of information may be desired in order to accurately search for patient medication history information. For example, if only a first name or only a last name of a patient are provided, it may be determined that the identification information for the patient is not sufficient. As another example, if no address is provided for a patient, it may be determined that the identification information for the patient is not sufficient. As yet another example, it may be determined that the identification information is not sufficient if no indication of patient consent to obtain medication history information is included in the request.

If it is determined at block 705 that the patient identification information is sufficient, then operations may continue at block 720. However, if it is determined at block 705 that the patient identification information is not sufficient, then operations may continue at block 710, and a request for additional patient identification information may be communicated to the healthcare service provider 108 (either directly or through a healthcare service provider hub). In response to the request made at block 710, a request for medication history information may be re-submitted by the healthcare service provider 108 at block 715 and operations may continue at block 705. Requests may be re-submitted as necessary until it is determined that the patient identification information is sufficient.

At block 720, at least a portion of the patient identification information may be utilized to search the medication history database 138. In this regard, medication history data stored in the medication history database 138 for the one or more patients may be located and/or identified. At block 725, a determination may be made as to whether any information for the one or more patients is located in the medication history database 138. If it is determined at block 725 that information for the one or more patients is located in the medication history database 138, then operations may continue at block 730 and the medication history information may be retrieved from the medication history database 138. If, however, it is determined at block 725 that no information for the one or more patients is located in the medication history database 138, then operations may continue at block 735.

At blocks 735-745, which may be optional in certain embodiments of the invention, information may be requested and received from one or more third party data sources, such as data sources 114. At block 735, medication history information for the one or more patients may be requested from one or more third party data sources 114. The requests may include at least a portion of the patient identification information, and the third party data sources 114 may utilize the patient identification information included in the requests to identify, locate, and/or retrieve medication history information for the one or more patients.

At block 740, patient medication history information may be received at the medication history service provider 110 from the one or more third party data sources 114. At block 745, any information retrieved from the medication history database 138 and the one or more third party data sources 114 may be aggregated and/or reconciled with one another. Duplicate information may be consolidated and/or deleted. Additionally, discrepancies in the information may be identified and processed. A wide variety of methods may be utilized as desired in various embodiments of the invention to process discrepancies. For example, all conflicted information may be included in a response to a request for patient medication history information. As another example, discrepancies may be identified and/or highlighted in a response. As yet another example, discrepancies may be resolved in an appropriate manner. One example of resolving discrepancies may be to determine that information received from a source that is deemed to be relatively more accurate or relatively more reliable is correct. Other methods for resolving discrepancies will be readily apparent to those skilled in the art.

As a result of the operations set forth in FIG. 7, requests for patient medication history information may be processed, the requested information may be identified and obtained if available, and the information may be aggregated together and formatted for communication to a requesting healthcare service provider 108. The method 700 may end following block 745.

The operations described in the method 700 of FIG. 7 do not necessarily have to be performed in the order set forth in FIG. 7, but instead may be performed in any suitable order. For example, in certain embodiments of the invention, information may be requested from the one or more third party data sources 114 prior to accessing the medication history database 138. Additionally, various operations described in the method 700 of FIG. 7 may be performed in a parallel manner. For example, in certain embodiments, requests may be communicated to the one or more third party data sources 114 in parallel with accessing the medication history database 138. Additionally, in certain embodiments of the invention, more or less than all of the operations set forth in FIG. 7 may be performed.

Figure 8:
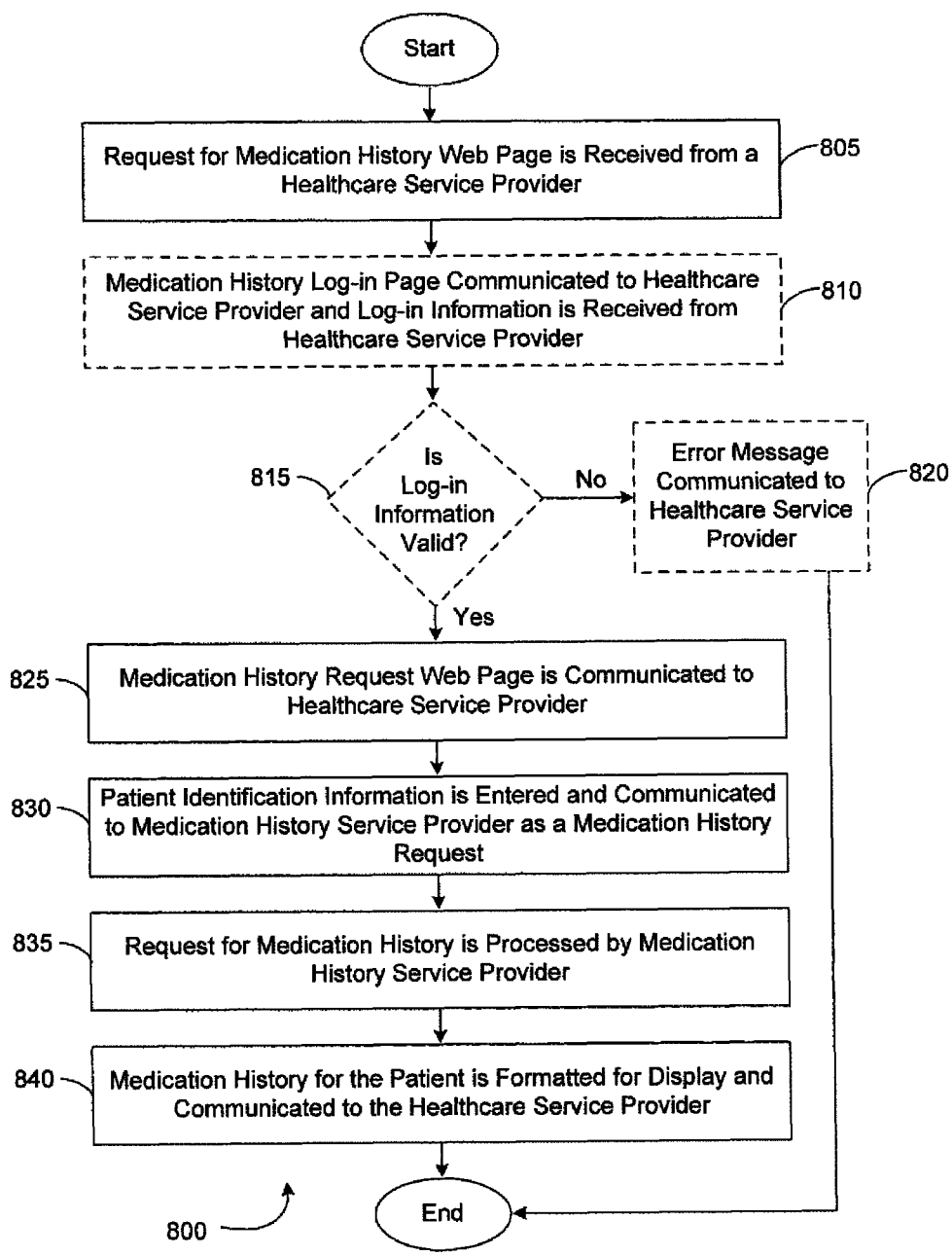
FIG. 8 illustrates an example flow diagram of a method for providing patient medication history, according to another example embodiment of the invention.

FIG. 8 illustrates an example flow diagram of a method 800 for providing patient medication history, according to another example embodiment of the invention. The method 800 may be utilized to receive and process requests for patient medication history that are made via a suitable web portal. A web server application may be hosted by a medication history service provider, such as, medication history service provider 110. A healthcare service provider, such as healthcare service provider 108, may utilize a suitable web access program, such as, a web browser, to access one or more web pages hosted by the web server application. These one or more web pages may facilitate the receipt of requests for patient medication history information and may further facilitate the communication and/or presentation of medication history information to the healthcare service provider 108. Examples of web pages that may be utilized in accordance with certain web based embodiments of the invention are described below with reference to FIGS. 9-14.

The method 800 may begin at block 805. At block 805, a request for a medication history web page may be received from a healthcare service provider 108. For example, an individual at the healthcare service provider 108 may utilize a web browser application to request a medication history web page from a web server associated with the medication history service provider 110. A uniform resource locator (URL) for the web page may be requested by the web browser application.

Following block 805, operations may continue at block 810. At block 810, which may be optional in certain embodiments of the invention, a medication history log-in web page may be communicated to the healthcare service provider 108. The log-in web page may include prompts for log-in information for the healthcare service provider 108 or for hospital service provider personnel. Log-in information may be entered into or linked to appropriate portions of the web page and communicated from the healthcare service provider 108 to the medication history service provider 110.

At block 815, which may also be optional in certain embodiments of the invention, a determination may be made as to whether the received log-in information is valid. If it is determined that the log-in information is invalid, then operations may continue at optional block 820 and an error message may be communicated to the healthcare service provider 108. Following communication of the error message at block 820, the method 800 may end. Alternatively, log-in information may be re-entered by the healthcare service provider 108 and communicated to the medication history service provider 110 for verification. If, however, it is determined at block 815 that the received log-in information is valid, then operation may continue at block 825.

At block 825, a medication history request web page may be communicated to the healthcare service provider 108 by the medication history service provider 110. The medication history request web page may include prompts for patient identification information. An example of a medication history request web page is described below with reference to FIG. 9. At block 830, patient identification information for one or more patients may be entered into the medication history request web page and communicated to the medication history service provider 110 as a request for patient medication history information.

The request for patient medication history information may be processed at by the medication history service provider 110 at block 835. One example of a method that may be utilized to process the request is described above with reference to FIG. 7. As a result of processing the request, medication history information for the one or more patients may be obtained from a medication history database, such as database 138, and/or from one or more third party data sources, such as data sources 114. The obtained information may also be aggregated and de-duplicated in certain embodiments of the invention. At block 840, the medication history information for the one or more patients may be formatted for display and communicated to the healthcare service provider. The medication history information may be communicated to the healthcare service provider in one or more suitable web pages. Examples of suitable web pages for displaying medication history information are described below with reference to FIGS. 10 and 11. Additionally and/or alternatively, the medication history information may be communicated to the healthcare service provider in one or more electronic files, such as, word files, .pdf files, database files, text files, etc.

The operations described in the method 800 of FIG. 8 do not necessarily have to be performed in the order set forth in FIG. 8, but instead may be performed in any suitable order. Additionally, in certain embodiments of the invention, more or less than all of the operations set forth in FIG. 8 may be performed. For example, in certain embodiments of the invention, web pages and/or web page requests may be communicated through or routed through a healthcare service provider hub or aggregator, such as healthcare service provider hub 112.

In various embodiments of the invention, patient medication information may be requested and/or received via one or more suitable web pages. A wide variety of different web pages may be utilized as desired in web-based embodiments of the inventions. A few examples of suitable web pages are provided in FIGS. 9-14; however, it will be appreciated that numerous other web pages and/or web page formats may be utilized in accordance with embodiments of the invention.

Figure 9:
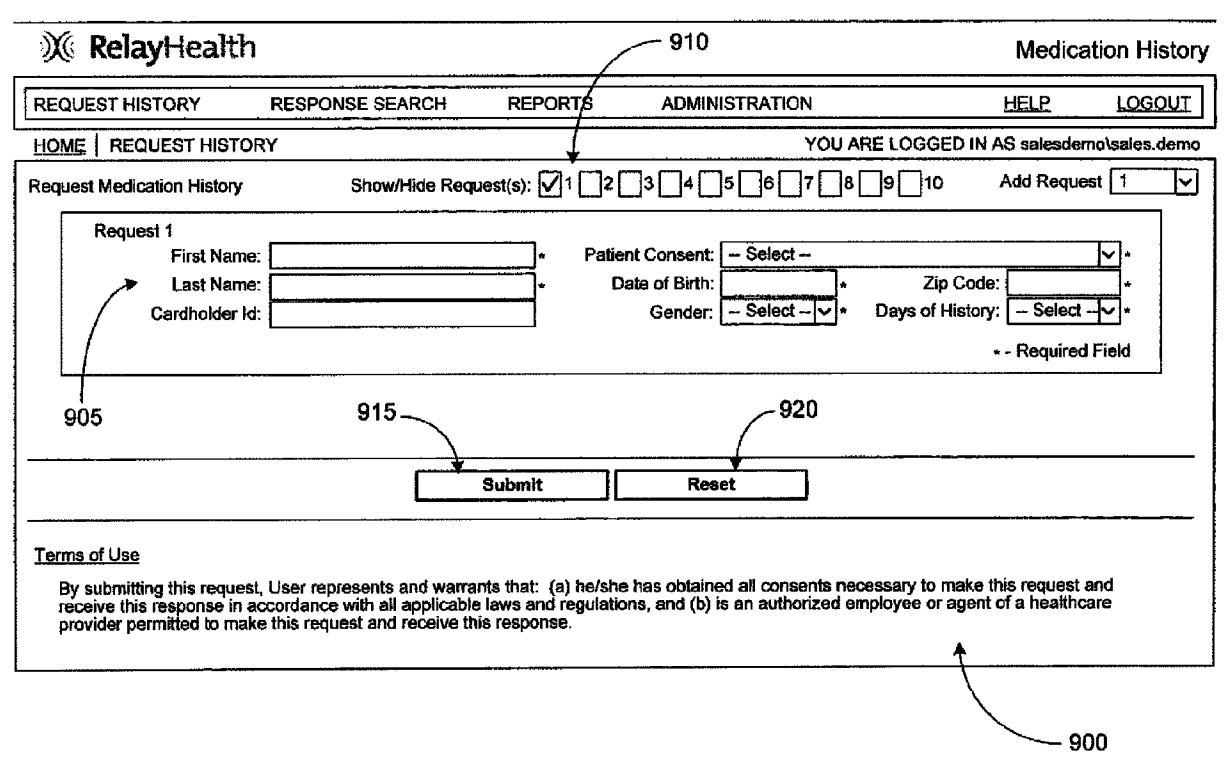

FIG. 9 illustrates an example web page 900 that facilitates the receipt of patient medication history requests, according to an example embodiment of the invention. The web page 900 may include one or more prompts and associated fields 905 for the receipt of patient identification information. A wide variety of different types of patient identification information may be received. As shown in FIG. 9, patient identification information may be received for a patient's first name, last name, insurance cardholder identification, date of birth, gender, and zip code. Additionally, an indication of whether the patient consents to the medication history request may be entered. As shown, the consent indication may be entered via a pull down menu; however, the consent indication may be entered in a wide variety of ways, such as, a pull down menu, check boxes, etc. Additionally, an indication for a period for which patient medication history is desired may be entered. Patient medication history may be requested for any time period. In certain embodiments of the invention, desired date ranges may be entered. In other embodiments of the invention, a look back period may be entered and/or selected. A wide variety of different look back periods may be entered and/or selected as desired in various embodiments of the invention. For example, medication history may be requested for the previous month, the previous year, etc. As shown in FIG. 9, a look back period may be requested via a pull down menu.

Additionally, in certain embodiments of the invention, identification information may be entered for multiple patients. A web page user may utilize appropriate check boxes 910 to enter and/or display identification information and/or the results of requests entered for additional patients. Once patient identification information is entered for one or more patients, a submit button 915 may be selected in order to submit the patient medication history request. Alternatively, a reset button 920 may be selected to clear patient identification information from the web page 900.

Figure 10:
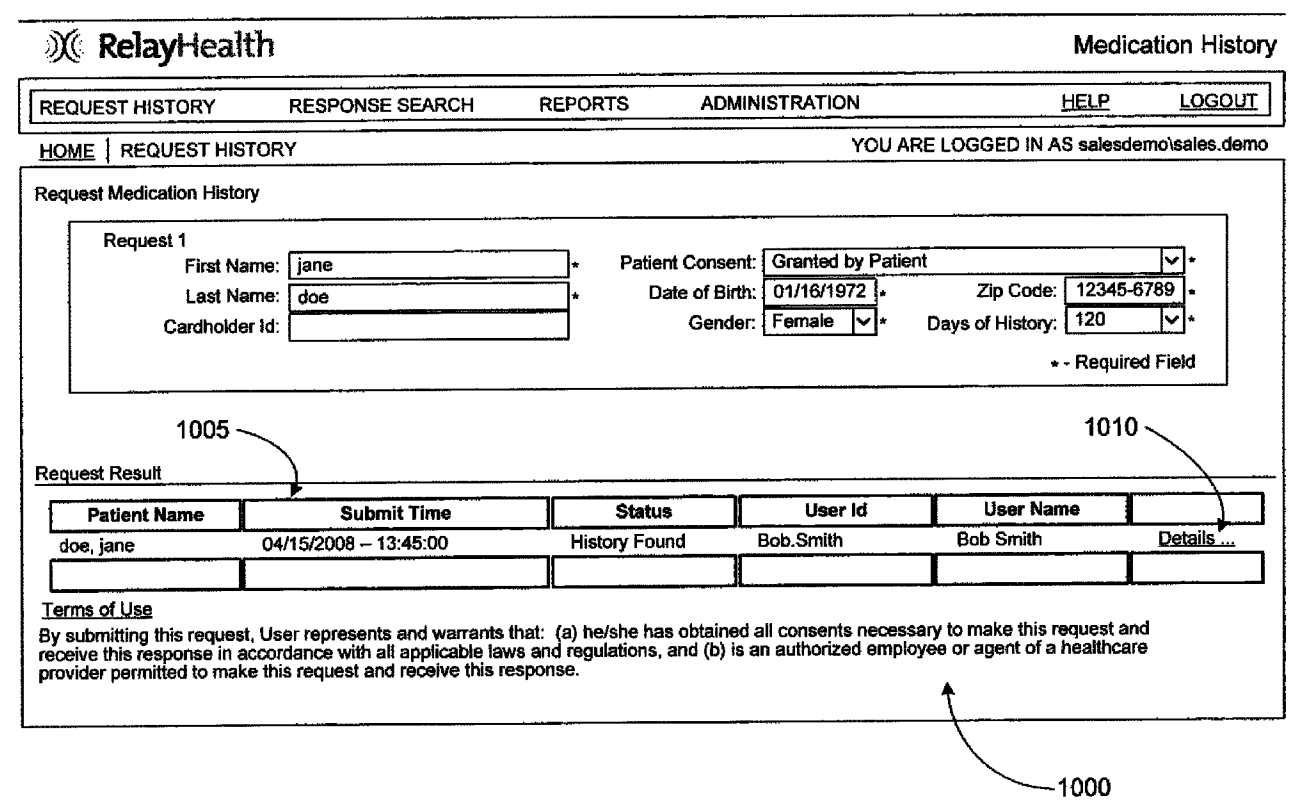

FIG. 10 illustrates an example web page 1000 for displaying the results of a patient medication history request, according to an example embodiment of the invention. With reference to FIG. 10, the entered patient identification information may be displayed along with information 1005 associated with the results of the request. The results may include, but are not limited to, identification information associated with the search and/or the patient, a date and time that the request was submitted, an indication as to whether medication history information was identified, and/or identification information associated with the requested healthcare service provider or healthcare service provider personnel. Additionally, a hyperlink 1010 may be provided that facilitates the display and/or receipt of detailed medication history information for the patient. Selection of the hyperlink may facilitate a download of the information and/or the display of a suitable web page for displaying the information, such as, the web page shown in FIG. 11 and discussed in greater detail below.

FIG. 11 illustrates an example web page 1100 for displaying detailed medication history information for a patient, according to an example embodiment of the invention. With reference to FIG. 10, patient identification information 1105 for the patient may be displayed along with information 1110 associated with the medication history of the patient. The medication history information 1110 may additionally be sorted utilizing a wide variety of different sorting criteria 1115. For example, the medication history information may be sorted by drug name, drug manufacturer, claim date, third-party processing system or other adjudication system, pharmacy, etc. and/or by a combination of criteria. Additionally, print and/or export or download options 1120 may be provided that facilitate formatting the medication history for printing and/or downloading the medication history information to a suitable memory associated with the healthcare service provider 108. The medication history information may be downloaded and/or exported in a wide variety of different formats as desired (e.g., .pdf, etc.)

Figure 12:
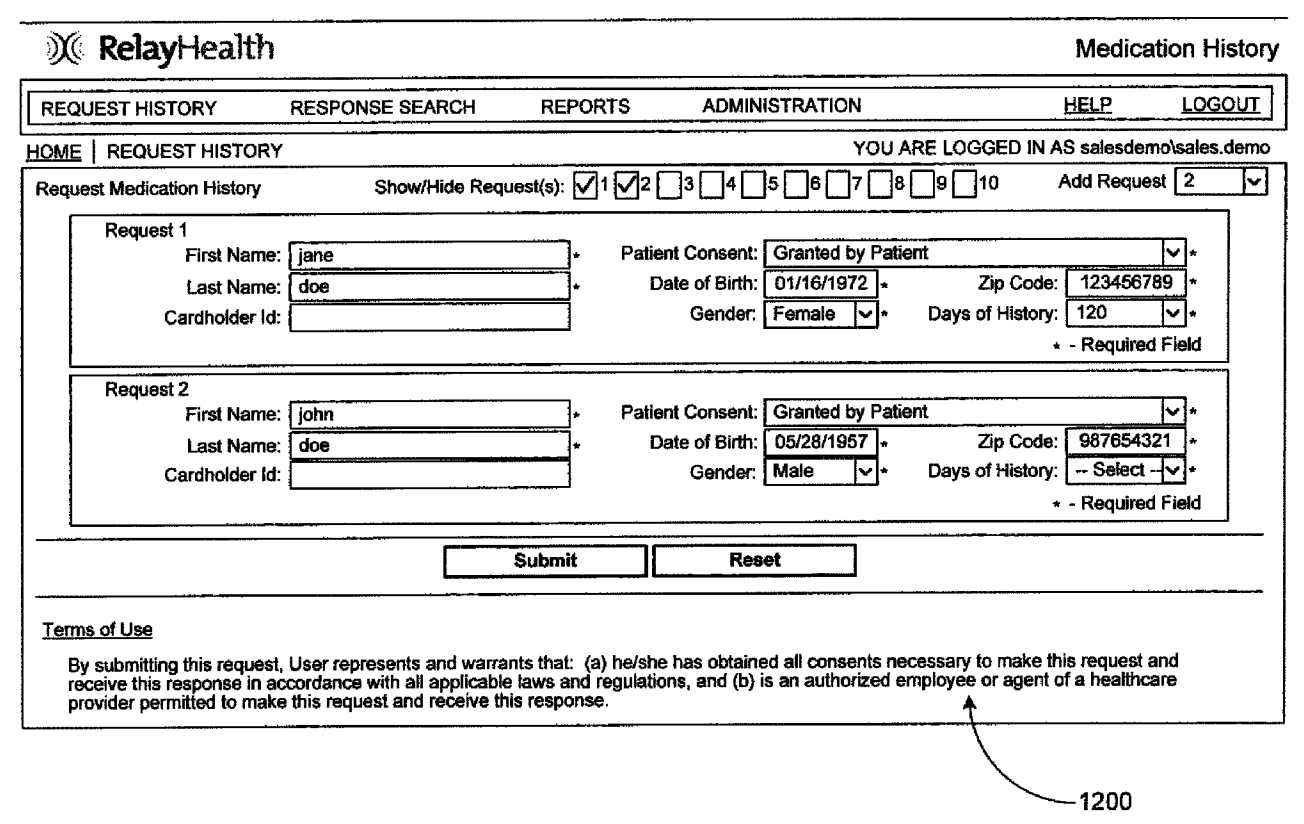

FIG. 12 illustrates another example web page 1200 for receiving patient medication history requests, according to an example embodiment of the invention. FIG. 12 is similar to FIG. 9; however, in FIG. 12, the entry of patient identification information is illustrated. Additionally, the entry of patient identification information is illustrated for a plurality of patients.

Figure 13:
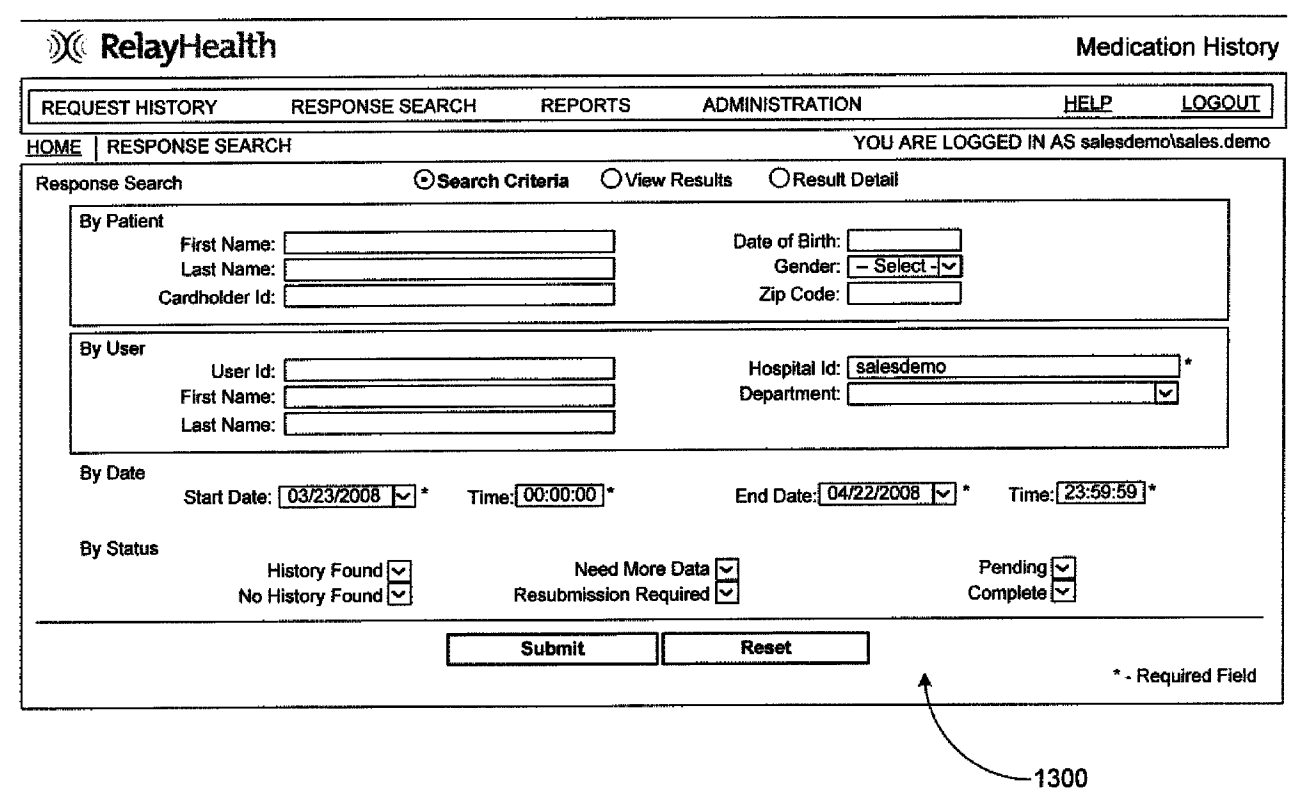

FIG. 13 illustrates an example web page 1300 for sorting and/or sorting patient medication history information, according to an example embodiment of the invention. For example, patient medication history information received from the medication history service provider 110 in response to a plurality of requests for the information may be searched and/or sorted. Patient medication history information may be searched and or sorted by utilizing a wide variety of different criteria. Examples of various criteria are illustrated in FIG. 13 and include, but are not limited to, patient identification information (e.g., name, insurance information, date of birth, gender, etc.), user information for health care service provider personnel submitting the request (e.g., user name, name, hospital identification, department, etc.), date, time, ranges of dates and/or times, and/or the status of a search request. A wide variety of statuses may be assigned to various search requests, for example, medication history found, no medication history found, need more patient identification information, re-submission of the request is required, request is pending, and/or request is complete. Additionally, more than one status indicator may apply to a search request.

Figure 14:
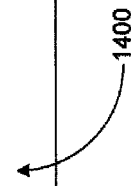
FIG. 14 illustrates an example web page for displaying the results of a sort of patient medication history, according to an example embodiment of the invention.

FIG. 14 illustrates an example web page 1400 for displaying the results of a search or sort of patient medication history information, according to an example embodiment of the invention. As shown in FIG. 14, information associated with a plurality of requests for patient medication history information may be sorted in accordance with one or more different criteria, such as, the criteria described above with reference to FIG. 13. For each request, a hyperlink may be provided that facilitates the display and/or receipt of detailed medication history information associated with the request. Selection of the hyperlink may facilitate a download of the information and/or the display of a suitable web page for displaying the information, such as, the web page shown in FIG. 11 and discussed in greater detail above.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for providing medication history information of a patient, the method comprising the following steps implemented by one or more computers:

receiving, from a plurality of pharmacies by a switch provider system comprising the one or more computers, a plurality of respective pharmacy claim transactions for a patient;

processing, by the switch system, the plurality of claim transactions to facilitate routing of the claim transactions to a plurality of claims adjudicators and routing of responses to the claim transactions from the plurality of claims adjudicators to the plurality of pharmacies;

storing, by the switch system as the claims are processed by the switch system, information associated with at least one of (i) the claim transactions or (ii) the responses to the claims transactions as medication history information for the patient;

receiving, by a switch provider system from a healthcare service provider or from a healthcare service provider aggregator associated with the healthcare service provider, a request for medication history of the patient, the request comprising identification information for the patient;

accessing, by the switch provider system utilizing at least a portion of the patient identification information, at least a portion of the stored medication history information; and aggregating, by the switch provider system, at least a portion of the accessed medication history information with patient medication history information received from one or more third party data sources corresponding to respective queries to the one or more third party data sources, communicating, by the switch provider system, the aggregated information in response to the received request.

2. The method of claim 1, wherein the identification information for the patient comprises one or more of a name of the patient, a zip code of the patient, a gender of the patient, a date of birth for the patient, or insurance information associated with the patient.

3. The method of claim 1, wherein the request is received from the healthcare service provider and the aggregated information is communicated to the healthcare service provider in response to the received request.

4. The method of claim 1, wherein the request is received from the healthcare service provider aggregator associated with the healthcare service provider, and the aggregated information is communicated to the healthcare service provider aggregator.

5. The method of claim 1, further comprising:
communicating, by the switch provider system, one or more respective queries for medication history information associated with the patient to the one or more third party data sources; and
receiving, by the switch provider system, the patient medication history information from the one or more third party data sources.

6. The method of claim 1, wherein receiving a request for the medication history of the patient comprises receiving a request via a world wide web based application.

7. A switch provider system comprising:
at least one network interface configured (i) to receive, from a plurality of pharmacies, a plurality of respective pharmacy claim transactions for a patient, (ii) to communicate the claim transactions to a plurality of claims adjudicators, (iii) to receive, from the plurality of claims adjudicators, respective responses to the claim transactions, (iv) to communicate the responses to the plurality of pharmacies, (v) to receive, a request from a healthcare service provider for the medication history of the patient, the request comprising identification information for the patient, and (vi) to communicate aggregated medication history information for the patient to the healthcare service provider;
at least one memory comprising a medication history database, the medication history database comprising stored medication history information associated with at least one of (i) the claim transactions or (ii) the responses to the claim transactions; and
at least one computer processor configured (i) to process the claim transactions and the responses, (ii) to direct communication of the claim transactions and the responses, (iii) to direct, during the processing, storage of the medication history information in the medication history database, (iv) to access, utilizing at least a portion of the patient identification information, the medication history information from the medication history database, (v) aggregate at least a portion of the information accessed from the medication history database with patient medication history information received from one or more third party data sources corresponding to respective queries to the one or more third party data sources, and (vi) to direct communication of the aggregated information to the healthcare service provider in response to the received request.

8. The system of claim 7, wherein the identification information for the patient comprises one or more of a name of the patient, a zip code of the patient, a gender of the patient, a date of birth for the patient, or insurance information associated with the patient.

9. The system of claim 7, wherein the at least one computer processor is further configured to direct communication of the respective queries for medication history information associated with the patient to the one or more third party data sources and to receive the patient medication history information from the one or more third party data sources.

10. The system of claim 9, wherein each of the one or more third party data sources is associated with a prescription benefit manager, a pharmacy switch provider, a pharmacy benefit manager, an insurance company, or a healthcare coverage company.

11. The system of claim 7, wherein the at least one computer processor receives the request for medication history information via a world wide web based application.

12. The system of claim 9, wherein the at least one computer processor is configured to access the medication history database in parallel with directing communication of the queries for patient medication history information to one or more third party data sources.

13. A method for providing patient medication history information, the method comprising the following steps implemented by one or more computers:
switching, by a switch provider system comprising one or more computers, a plurality of pharmacy claim transactions and associated adjudicated responses for a patient between a plurality of pharmacies and at least one claims adjudicator, wherein the switching comprises;
receiving, from a plurality of pharmacies by the switch provider system, a plurality of respective pharmacy claim transactions for a patient; and
processing, by the switch provider system, the plurality of pharmacy claim transactions to facilitate routing of the pharmacy claim transactions to a plurality of claims adjudicators and routing of responses to the pharmacy claim transactions from the plurality of claims adjudicators to the plurality of pharmacies;
storing, by the switch provider system, information associated with at least one of (i) the pharmacy claim transactions or (ii) the responses to the claims transactions as medication history information for the patient;
receiving, by the switch provider system from a healthcare service provider or from a healthcare service provider aggregator associated with the healthcare service provider, a request for medication history of the patient, the request comprising identification information for the patient;
utilizing, by the switch provider system, at least a portion of the identification information to access the stored information associated with the plurality of switched pharmacy claim transactions;

obtaining, by the switch provider system, at least a portion of the stored medication history information; and aggregating, by the switch provider system, at least a portion of the obtained medication history information with patient medication history information received from one or more third party data sources corresponding to queries to the third party data sources; and communicating, by the switch provider system, the aggregated information in response to the received request.

14. The method of claim 13, wherein the stored information for each of the plurality of switched pharmacy claim transactions comprises at least one of a name of a patient associated with the pharmacy claim transaction, a zip code of the patient, a gender of the patient, a date of birth for the patient, or insurance information associated with the patient.

15. The method of claim 13, wherein the received identification information for the patient comprises one or more of a name of the patient, a zip code of the patient, a gender of the patient, a date of birth for the patient, or insurance information associated with the patient.

16. The method of claim 13, wherein the request is received from a healthcare service provider and the at least a portion of the stored information is communicated to the healthcare service provider or the healthcare service provider aggregator in response to the received request.

17. The method of claim 13, further comprising:

communicating, by the switch provider system, the respective queries for medication history information associated with the patient to the one or more third party data sources; and receiving, by the switch provider system, the patient medication history information from the one or more third party data sources.

* * * * *

UNITED STATES PATENT AND TRADEMARK OFFICE
CERTIFICATE OF CORRECTION

PATENT NO. : 8,538,777 B1
APPLICATION NO. : 12/165031
DATED : September 17, 2013
INVENTOR(S) : Elizabeth S. Kaye et al.

Page 1 of 1

It is certified that error appears in the above-identified patent and that said Letters Patent is hereby corrected as shown below:

In the Claims

At column 23, line 60, delete "service" and insert -- switch --.

Signed and Sealed this
Third Day of December, 2013

Margaret A. Focarino
*Commissioner for Patents of the United States Patent and Trademark Office*